United States Patent
Silva et al.

(10) Patent No.: US 7,582,140 B2
(45) Date of Patent: Sep. 1, 2009

(54) BIOGAS FUEL CONDITIONING SYSTEM

(75) Inventors: Joseph A. Silva, Poway, CA (US); John Scalone, La Mesa, CA (US); Jeffrey E. Silva, San Diego, CA (US); Thomas L. Moore, Georgetown, MA (US)

(73) Assignee: Bio Spark LLC, San Diego, CA (US)

( * ) Notice: Subject to any disclaimer, the term of this patent is extended or adjusted under 35 U.S.C. 154(b) by 0 days.

(21) Appl. No.: 11/811,631

(22) Filed: Jun. 11, 2007

(65) Prior Publication Data

US 2007/0289448 A1   Dec. 20, 2007

Related U.S. Application Data

(60) Provisional application No. 60/813,529, filed on Jun. 14, 2006.

(51) Int. Cl.
 *B01D 46/00* (2006.01)
(52) U.S. Cl. .................. 95/273; 55/467.1; 55/490.1; 55/490.2; 95/288
(58) Field of Classification Search .............. 95/273, 95/288, 467.1, 490.1, 490.2; 62/617, 642; 60/39.465, 465; 55/467.1, 490.1, 490.2
See application file for complete search history.

(56) References Cited

U.S. PATENT DOCUMENTS

| 4,267,702 | A  | * | 5/1981 | Houk ........................... 62/115 |
| 6,772,607 | B2 | * | 8/2004 | Tsuboe et al. ................. 62/510 |
| 6,865,877 | B2 | * | 3/2005 | Yoshida et al. ........... 60/39.465 |
| 2006/0168998 | A1 | * | 8/2006 | Chin et al. .................... 62/515 |

FOREIGN PATENT DOCUMENTS

AT   EP 1527808 A1 *  5/2005

* cited by examiner

*Primary Examiner*—Duane Smith
*Assistant Examiner*—Ives Wu

(57) ABSTRACT

A biogas treatment system removes moisture and other unwanted materials from biogas originating, for example, with a landfill or anaerobic digester. Water and other unwanted materials are thus removed from landfill gas and waste water biogas, while the gas temperature is controlled to a usable level. More especially, the present invention provides for the removal of water and other unwanted ingredients of biogas with a greatly reduced energy requirement when compared to conventional technologies.

18 Claims, 3 Drawing Sheets

BIOGAS FUEL CONDITIONING SYSTEM

CROSS REFERENCE TO RELATED APPLICATION

Figure 1:
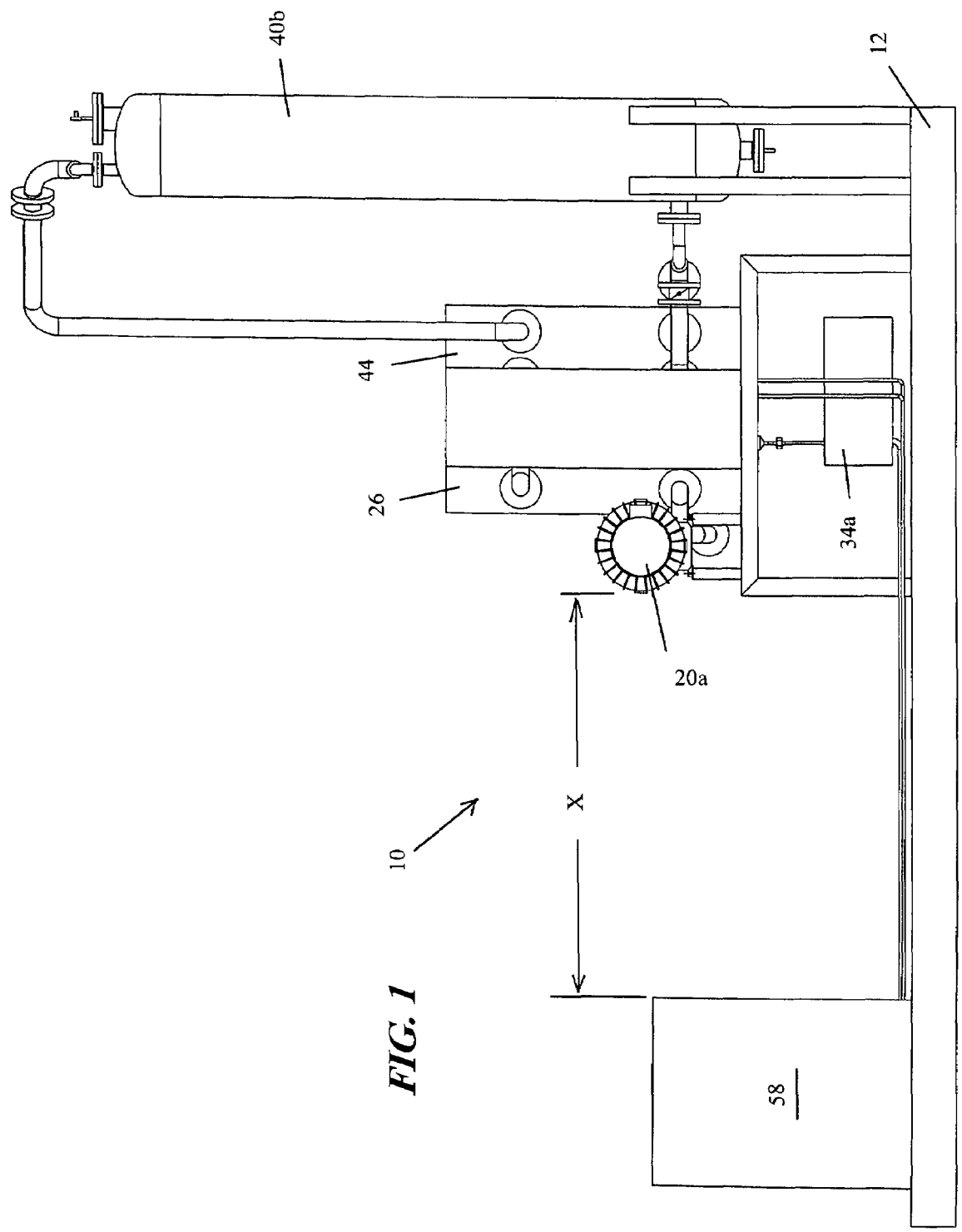

This application is related to, and claims benefit of and priority under 35 USC §119(c) from U.S. provisional application No. 60/813,529, filed 14 Jun. 2006.

FIELD OF THE INVENTION

The present invention relates to the removal of moisture and other unwanted materials from biogas. That is, water and other unwanted materials are removed from landfill gas and waste water biogas. More particularly, the present invention provides for the removal of these unwanted ingredients of the biogas with a greatly reduced energy requirement than conventional technology.

RELATED TECHNOLOGY

Conventionally, the treatment of methane gas from various sources, such as waste water treatment anaerobic digesters, and from landfills, have posed significant technical difficulties. That is, the proper conditioning of methane gas from these sources in order to reduce water and levels of unwanted compounds to a level that is acceptable to burn in various equipment has been problematical. Equipment which may employ such biogas if properly prepared for use, includes internal combustion engines, boilers, micro-turbines, turbines, and most recently Fuel Cells.

But, the conventional treatment processes have been expensive, the results have varied greatly from marginal to somewhat acceptable and the energy requirement has been very high.

SUMMARY OF THE INVENTION

In view of the deficiencies of the related technology, it is an object for this invention to ameliorate or eliminate one or more of these deficiencies.

It is another object of the invention to lower treated biogas temperature and reheat the gas through a single heat exchanger system. This effectively cools the incoming biogas and reheats the exiting biogas simultaneously.

Another object of the invention is to reduce the chiller size needed to lower the gas temperature to the appropriate level and do this while reducing the energy required.

It is another object of the invention to reheat the biogas after chilling it back to a temperatures that contains a minimum of 30 degrees superheat above the biogas dew point to insure maximum life for subsequent equipment utilizing the biogas because no further moisture can drop out of the biogas.

It is another object of the invention to use direct chilling of the biogas in a heat exchanger to simplify the system, reduce system cost and reduce electrical load.

It is another object of the invention to be able to treat varying flows and pressures of biogas while maintaining a minimum dew point of at least 34° F. and then increase the biogas temperature to a minimum of 30° F. of reheat/superheat above the dew point at the point of delivery automatically under varying conditions.

Accordingly, an embodiment of the present invention provides a fuel treatment system that addresses moisture removal, accomplishes removal of other unwanted ingredients of the biogas, and reheats the biogas gas to most effectively protect any media system used to remove those additional contaminants.

This inventive device or system offers the following salient features:
Consumes less energy than conventional systems;
is far less complicated than conventional systems;
is less expensive; and
addresses the critical biogas reheat/superheat requirements to protect the media systems employed to remove other unwanted ingredients of the biogas.
Automatically maintains the biogas reheat/superheat within a desired range at the point of delivery under varying conditions.

BRIEF DESCRIPTION OF THE DRAWING FIGURES

Figure 2:
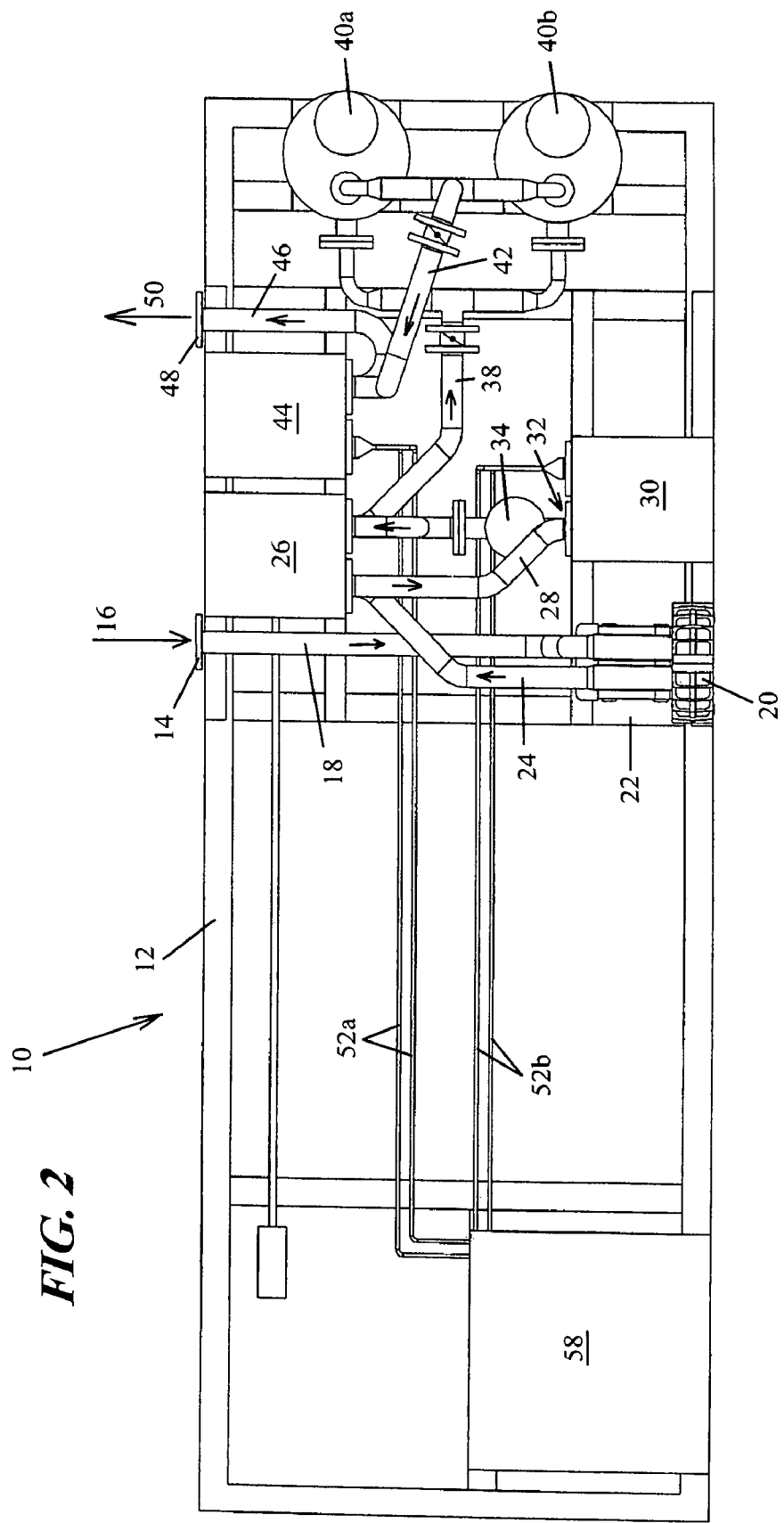
Figure 3:
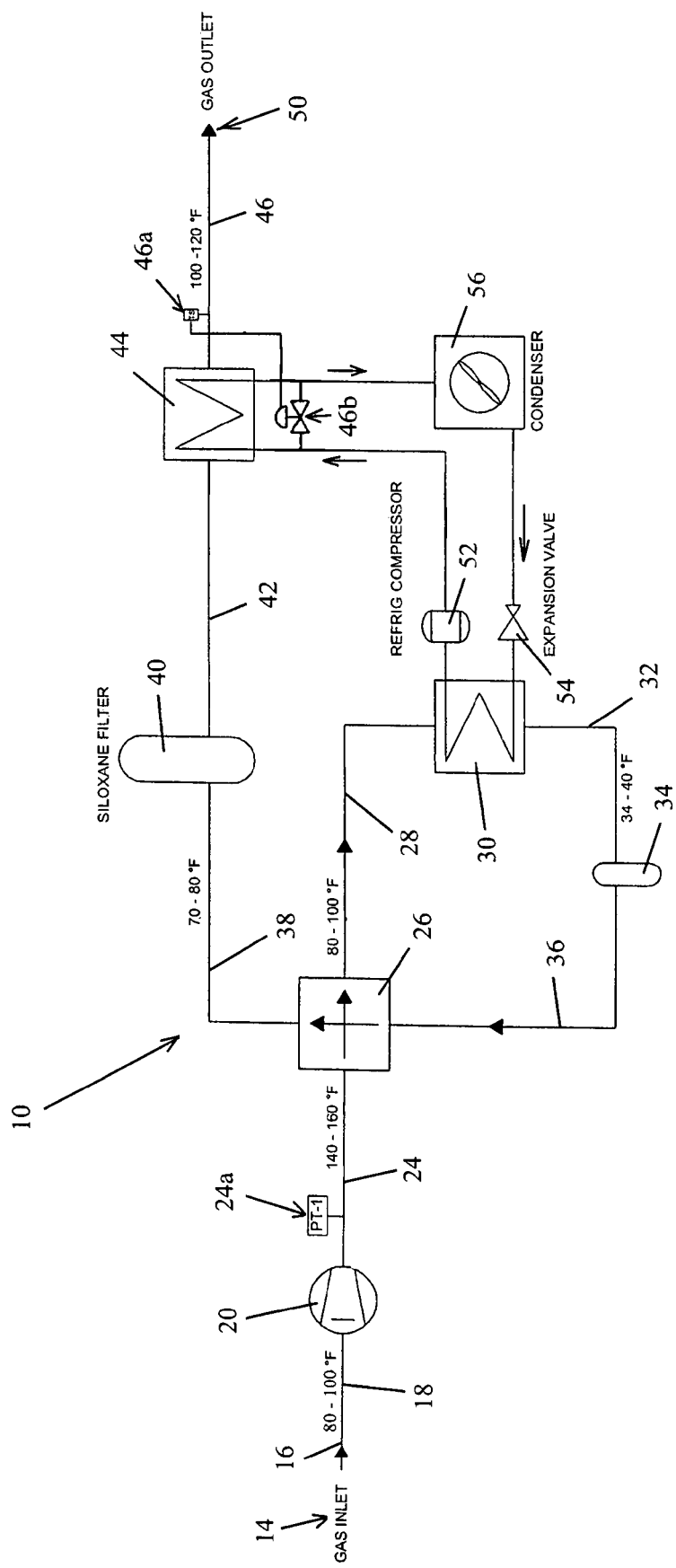

FIG. 1 provides an elevation view of a biogas treatment device according to this invention;

FIG. 2 is an plan view of the biogas treatment device seen in FIG. 1; and FIG. 3 provides a diagrammatic or schematic flow diagram of the device seen in FIGS. 1 and 2.

DETAILED DESCRIPTION OF AN EXEMPLARY PREFERRED EMBODIMENT

In the present invention for conditioning biogas, we first utilize a blower to increase the pressure of the biogas. This has the effect of insuring that the treated biogas is delivered from the treatment system at a sufficient pressure (i.e., offsetting pressure drops occasioned by components of the treatment system), effectively lowers the dew point of the biogas slightly, and increases the temperature of the biogas. Next, in a gas-to-gas heat exchanger we pre-cool the incoming gas prior to it entering a refrigeration-cycle gas dryer to significantly lower the required chilling load and the size of the chiller required.

Thirdly, the biogas is then exposed in a refrigerant-to-gas heat exchanger to liquid refrigerant in a heat exchanger which on the biogas side has the effect of lowering the gas temperature well below its dew point.

Subsequently, we utilize a coalescing filter which filters out the condensed moisture. Next, we utilize the chilled biogas to absorb heat in the gas-to-gas heat exchanger described above, significantly reducing energy requirements for the system, and increasing the temperature of the biogas. Next, we employ a siloxane filter to remove unwanted compounds from the biogas.

Finally, we employ a gas-to-refrigerant heat exchanger to on the one hand, apply reheat to the biogas, and on the other hand, to serve as at least a significant part of the condenser function for the refrigerant cycle, again greatly reducing the energy requirements for the system. Additionally, this provides an automatic or inherent function that serves to maintain the biogas reheat/superheat within a desired range at the point of delivery from the system under varying conditions. Any additional refrigerant condensing function which is required by the refrigeration equipment is performed by a refrigerant-to-ambient air condenser. A temperature sensor senses the temperature (reheat/superheat) of the treated biogas downstream of the gas-to-refrigerant heat exchanger, and controls a regulator valve setting which controls the amount of refrigerant condensation taking place by heat transfer to the biogas, and thus controlling the temperature of the treated biogas so that it does not exceed the temperature permitted by subsequent equipment which will utilize the biogas to produce energy. This also ensures that there is a minimum of 30° F. of reheat/superheat for the biogas under varying conditions. In comparison to the conventional technology, the present invention reduces the parasitic load by 87%.

An example and overview of the method carried out by the present invention follows: digester gas enters a system according to the present invention at a temperature range between 80-100° F. through a blower which (due to compression) increases the temperature to about 140-160° F. The biogas then moves into the first heat exchanger which lowers the temperature of the biogas from a range of 140° F. to 160° F. down to about 80° F. to 100° F. After the biogas exits this first heat exchanger it flows into a chilling heat exchanger cooled by refrigerant, which lowers the gas temperature to a range between 34° F. and 40° F. This chilling process condenses the moisture out of the biogas stream. The biogas next enters a coalescing filter which filters out the condensed moisture. After the moisture is removed from the biogas stream, it is reheated as it travels back through the first heat exchanger and picks up heat from the incoming biogas. This first heat exchanger thus increases the biogas temperature up to a range between about 75° F. to 80° F. thus raising it approximately 35° F. above the dew point. The result is that substantially dry biogas is provided. The treated gas has a minimum of 30° F. superheat. By ensuring that all moisture is removed from the biogas by cooling the gas to a low dew point then reheating the gas there is no moisture contained within the gas to mix with Carbon Dioxide (Co2) and Hydrogen Sulfide (H2S) which could form Carbonic and/or Hydrochloric acid within the system. A siloxane filter is utilized to remove these components from the biogas stream.

Turning now to FIGS. 1-3 considered in conjunction with one another, it is seen in FIGS. 1 and 2 that a system or device 10 for treating wet biogas is carried on a base or skid 12, resulting in the system 10 being a unitary facility, which may be shipped and installed easily. At a flanged connection 14 (best seen in FIG. 2), a wet biogas stream 16 enters the apparatus 10, and travels along pipe 18 to a variable-speed blower 20. This blower 20 is driven by a variable-speed motor 22 (best seen in FIG. 2), and the wet biogas exits the blower along pipe 24. As is illustrated in FIG. 3, a pressure transducer 24a is associated with the pipe 24 and provides an input signal to a speed control (not show in the drawing Figures) controlling the speed of motor 22 such that a desired pressure level for the wet biogas is maintained in the pipe 24.

Pipe 24 supplies the pressurized wet biogas to first gas-to-gas heat exchanger 26. In the heat exchanger 26, the wet biogas gives up heat to dry biogas, as will be further explained. From the heat exchanger 26, cooled wet biogas flows along pipe 28 to a gas-to-refrigerant heat exchanger (i.e., a refrigerant evaporator) 30. In the evaporator 30 the wet biogas is chilled to a temperature well below its dew point, so that moisture in the biogas forms droplets. The chilled but still wet biogas flows from the evaporator 30 along pipe 32 (best seen in FIG. 3) to a coalescing filter 34, which separates the water droplets from the biogas stream. As is seen best in FIG. 3, the coalescing filter 34 drains the collected moisture (i.e., water) to a drain tank 34a, from which the water is periodically emptied. From the coalescing filter, the now dry biogas flows along pipe 36 to heat exchanger 26, where it absorbs heat from the incoming wet biogas stream. From heat exchanger 26, the now dry and re-warmed biogas flows in pipe 38 to a siloxane filter 40, which is preferably a set (i.e., a parallel pair of siloxane filter towers 40a and 40b). These towers remove unwanted compounds that might cause acid formations in equipment utilizing the treated biogas.

Next, the filtered dry biogas flows along pipe 42 to a refrigerant condenser heat exchanger 44 where reheat is applied to the dry biogas. This heat exchanger serves as a major part of the condensing facility for the refrigerating system. As will be seen, the degree of reheat and super heat of the dry biogas is controlled to a temperature acceptable to subsequent equipment (not seen in the drawing Figures) which will utilize the treated biogas. From the heat exchanger 44, the reheated dry biogas flow via a pipe 46 to a flange 48 and exits as a treated biogas stream 50. For the purpose of regulating the temperature of the treated biogas, a temperature sensor 46a is associated with the pipe 46, and controls a bypass valve 46b, so that increasing temperature of the biogas in pipe 46 progressively opens the bypass valve 46b to prevent this temperature from exceeding a determined level.

In order to complete this description of the system 10, it is to be noted that the refrigerant system includes in addition to the evaporator heat exchanger 30 and condenser heat exchanger 44, a refrigerant compressor 54, an expansion valve 54, and a supplemental condenser (i.e., an air-cooled condenser) 56. The compressor 54 and condenser 56 are housed in a housing 58, best seen in FIGS. 1 and 2, and these components are interconnected as seen in FIG. 3 by refrigerant piping 52a and 52b seen in FIG. 2. The housing 58 is preferably separated by a distance X (seen in FIG. 1) from the portions of the apparatus carrying combustible biogas, so that a commonly available refrigeration system and components may be utilized.

Having thus described the invention, what is desired to be protected by Letters Patent is presented in the subsequently appended claims. It is to be noted that the present inventive process also allows for variable gas flow through the system while maintaining the proper amount of cooling and reheating of the gas over a wide range of gas flows. This flexibility of the process and apparatus ensures that even at a maximum gas flow through the system the gas is cooled and reheated to the proper temperatures and ensures the gas is dry through out the range of flows. Also, the present inventive process incorporates a direct refrigeration system to cool the gas and to also reheat the gas thus ensuring through the thermodynamic process there will always be enough cooling to cool the available gas to the required temperature level and then to reheat the gas to the needed reheat level to ensure the gas will remain above the dew point under all conditions. Excess heat from the refrigeration process is dissipated to ambient air. Finally, the present inventive process also utilizes plate and frame heat exchangers to maximize the heat exchange efficiency of the system and to further lower parasitic loads. Since the plate and frame heat exchangers are utilized for accomplishing the gas cooling and reheating, additional plates can be added or removed to optimize the efficiency of the system.

What is claimed is:

1. An inventive biogas fuel conditioning apparatus for removal of moisture and other unwanted constituents from a wet biogas stream in order to supply dry conditioned biogas fuel to a fuel consumer, said apparatus comprising:

a blower, said receiving, pressurizing, and warming a wet biogas stream in order to provide a substantially constant-pressure biogas stream flow to the fuel consumer;

a first heat exchanger receiving and cooling the wet pressurized warm biogas stream from said blower;

a second heat exchanger receiving the cooled wet biogas stream from said first heat exchanger and further chilling the wet biogas stream to a predetermined temperature to condense substantially all moisture in the biogas stream;

a first filter receiving the chilled biogas stream from said second heat exchanger and removing the condensed moisture to provide a dry biogas stream;

said first heat exchanger then receiving and warming the dry biogas stream from said first filter by heat exchange with the incoming wet pressurized warm biogas stream; and a third heat exchanger further warming the dry biogas stream from said first heat exchanger;

wherein said second heat exchanger is of the direct refrigerant-evaporating type.

2. The apparatus of claim 1, wherein in said blower is a variable-speed blower.

3. The apparatus of claim 2, wherein said blower is variable over a sufficient speed range so as to maintain substantially constant pressure to a fuel consumer despite variable consumption flow to the fuel consumer.

4. The apparatus of claim 1, wherein, said third heat exchanger is of the direct refrigerant-condensing type.

5. An inventive biogas fuel conditioning apparatus for removal of moisture and other unwanted constituents from a wet biogas stream in order to supply dry conditioned biogas fuel to a fuel consumer, said apparatus comprising:

a blower, said receiving, pressurizing, and warming a wet biogas stream in order to provide a substantially constant-pressure biogas stream flow to the fuel consumer;

a first heat exchanger receiving and cooling the wet pressurized warm biogas stream from said blower;

a second heat exchanger receiving the cooled wet biogas stream from said first heat exchanger and further chilling the wet biogas stream to a predetermined temperature to condense substantially all moisture in the biogas stream;

a first filter receiving the chilled biogas stream from said second heat exchanger and removing the condensed moisture to provide a dry biogas stream;

said first heat exchanger then receiving and warming the dry biogas stream from said first filter by heat exchange with the incoming wet pressurized warm biogas stream; and a third heat exchanger further warming the dry biogas stream from said first heat exchanger;

wherein said second heat exchanger and said third heat exchanger are in refrigerant flow relation with one another.

6. The apparatus of claim 5, wherein said second and said third heat exchangers are in refrigerant flow relation with a refrigerant compressor.

7. The apparatus of claim 6, wherein said refrigerant compressor is separated by a determined distance from said blower.

8. A method of conditioning biogas for use by a biogas consumer, said method including sequential steps of:

flowing the biogas at a first temperature of about 80° F. to about 100° F. to a blower;

utilizing said blower to both increase the pressure of the biogas, while also increasing its temperature to a second temperature in the range of about 140° F. to 160° F.;

utilizing a first heat exchanger to lower the temperature of the biogas to a third temperature of about 80° F. to 100° F.;

flowing the biogas through a chilling heat exchanger cooled by refrigerant so as to lower the temperature of the biogas to a fourth temperature of about 34° F. to 40° F., and utilizing the decreased temperature of the biogas to condense unwanted water from the biogas;

flowing the biogas through a coalescing filter to substantially remove condensed water;

flowing the dry biogas again through the first heat exchanger in heat exchange relation with biogas entering this heat exchanger at said second temperature and exiting at said third temperature, to recover heat thus warming the biogas to a fifth temperature of a range between about 75° F. to about 80° F.;

utilizing heat transfer between the wet and dry biogas streams in said first heat exchanger to raise the temperature of the dry biogas toward a temperature approximately 35° F. above its dew point, so that substantially dry and superheated biogas is provided; and utilizing a siloxane filter to remove carbon dioxide (Co2) and hydrogen sulfide (H2S) from the biogas.

9. The method of claim 8, further including the step of using a direct refrigerant-condensing heat exchanger to transfer heat to said dry biogas stream downstream of said first heat exchanger and before delivery of said dry biogas to said biogas consumer in order to ensure as least 30° F. of superheat.

10. The method of claim 8 further including the step of using a variable-speed blower.

11. The method of claim 10 further including the step of varying the speed of said variable-speed blower so as to maintain a substantially constant pressure for said biogas consumer despite variation of biogas-consumption flow rate of said biogas consumer.

12. The method of claim 8 further including the steps of:

utilizing at said second heat exchanger a direct refrigerant-evaporating heat exchange;

utilizing at said third heat exchanger a direct refrigerant-condenser heat exchanger; and arranging said second and said third heat exchangers to be in refrigerant-exchange relation with one another.

13. A continuous-flow method of conditioning a biogas stream, said method including sequential steps of:

flowing a biogas stream at a first temperature to a blower;

utilizing said blower to increase the pressure of the biogas stream and also increasing the temperature of the biogas stream to a second temperature;

utilizing a first heat exchanger to lower the temperature of the biogas stream to a third temperature;

flowing the biogas stream through a chilling second heat exchanger lowering the temperature to a fourth temperature and condensing unwanted water;

flowing the biogas stream through a coalescing filter to substantially remove condensed water;

flowing the biogas stream again through the first heat exchanger in heat exchange relation with the biogas stream entering this heat exchanger at the second temperature and exiting at the third temperature, so as to recover heat in said heat exchanger and warming the biogas stream to a fifth temperature, so that said fifth temperature is above its dew point of the biogas stream, and thus providing a substantially dry biogas stream; and filtering carbon dioxide (Co2) and hydrogen sulfide (H2S) from the biogas stream;

further including the step of utilizing a direct refrigerant-evaporating type of heat exchanger as said second heat exchanger.

14. The method of claim 13, further including the step of utilizing a variable-speed blower.

15. The method of claim 14 further including the steps of varying the operating speed of said variable-speed blower over a sufficient speed range so as to maintain substantially constant pressure to a fuel consumer despite variable biogas consumption flow to the fuel consumer.

16. The method of claim 13 further including the step of using as a third heat exchanger through which said biogas stream flows downstream of said second heat exchanger, a direct refrigerant-condensing type of heat exchanger.

17. A continuous-flow method of conditioning a biogas stream, said method including sequential steps of:
   flowing a biogas stream at a first temperature to a blower;
   utilizing said blower to increase the pressure of the biogas stream and also increasing the temperature of the bio gas stream to a second temperature;
   utilizing a first heat exchanger to lower the temperature of the biogas stream to a third temperature;
   flowing the biogas stream through a chilling second heat exchanger lowering the temperature to a fourth temperature and condensing unwanted water;
   flowing the biogas stream through a coalescing filter to substantially remove condensed water;
   flowing the biogas stream again through the first heat exchanger in heat exchange relation with the biogas stream entering this heat exchanger at the second temperature and exiting at the third temperature, so as to recover heat in said heat exchanger and warming the biogas stream to a fifth temperature, so that said fifth temperature is above its dew point of the biogas stream, and thus providing a substantially dry biogas stream; and
   filtering carbon dioxide (Co2) and hydrogen sulfide (H2S) from the biogas stream;
   further including the step of arranging said second and a third heat exchangers in refrigerant flow relation with one another.

18. The method of claim 17 further including the steps of providing a third heat exchanger applying superheat to said biogas stream by direct refrigerant-condensation; and
   putting said second heat exchanger and said third heat exchanger in direct refrigerant flow relation with one another.

* * * * *